United States Patent
Heyer et al.

(10) Patent No.: US 9,308,337 B2
(45) Date of Patent: Apr. 12, 2016

(54) SYSTEM FOR QUANTIFYING THE DISCREPANCY BETWEEN A PATIENT RECEIVING ASSISTED BREATHING AND A CORRESPONDING ASSISTANCE DEVICE

(75) Inventors: Laurent Heyer, Paris (FR); Pierre Baconnier, Grenoble (FR)

(73) Assignee: ASSISTANCE PUBLIQUE-HOPITAUX DE PARIS, Paris (FR)

( * ) Notice: Subject to any disclaimer, the term of this patent is extended or adjusted under 35 U.S.C. 154(b) by 1024 days.

(21) Appl. No.: 13/127,195

(22) PCT Filed: Nov. 3, 2009

(86) PCT No.: PCT/FR2009/052121
§ 371 (c)(1),
(2), (4) Date: Aug. 23, 2011

(87) PCT Pub. No.: WO2010/061092
PCT Pub. Date: Jun. 3, 2010

(65) Prior Publication Data
US 2011/0301481 A1    Dec. 8, 2011

(30) Foreign Application Priority Data
Nov. 3, 2008    (FR) ...................................... 08 57451

(51) Int. Cl.
*A61B 5/08*    (2006.01)
*A61M 16/00*    (2006.01)

(52) U.S. Cl.
CPC ... *A61M 16/0051* (2013.01); *A61M 2016/0027* (2013.01); *A61M 2016/0036* (2013.01)

(58) Field of Classification Search
CPC combination set(s) only.
See application file for complete search history.

(56) References Cited

FOREIGN PATENT DOCUMENTS

| WO | WO2004002561 | * | 1/2004 |
| WO | WO2004/002561 | | 8/2004 |
| WO | WO2008/116318 | | 10/2008 |

OTHER PUBLICATIONS

Rabarimanantsoa, H. et al., "Recurrence Plots and Shannon Entropy for a Dynamical Analysis of Asynchronisms in Noninvasive Mechanical Ventilation" CHAOS 17, 013115 2007 (Rabarimanantsoa).*
Letellier, C., et al. "Recurrence Plots for Dynamical Analysis of Non-Invasive Mechanical Ventilation" Phil. Trans. R. Soc. A (2008) 366, 621-634 (Letellie).*

* cited by examiner

*Primary Examiner* — Michael Kahelin
*Assistant Examiner* — Mitchell E Alter
(74) *Attorney, Agent, or Firm* — Blank Rome LLP

(57) ABSTRACT

This system is characterized in that includes:
  means (20) for acquiring information relating to the respiratory state of the patient (1) over a breathing cycle,
  means (21) for acquiring information relating to the operating state of the assistance device (2) over a mechanical cycle,
  means for filtering (22) and for processing (23) this information in order to detect and localize the changes in states of the patient over a breathing cycle and of the device over a mechanical cycle,
  means (24) for calculating a piece of information on desynchronization between the patient and the device from these changes in states, and
  means (25) forming a man/machine interface for returning this piece of desynchronization information to an operator.

18 Claims, 3 Drawing Sheets

Figure 1:
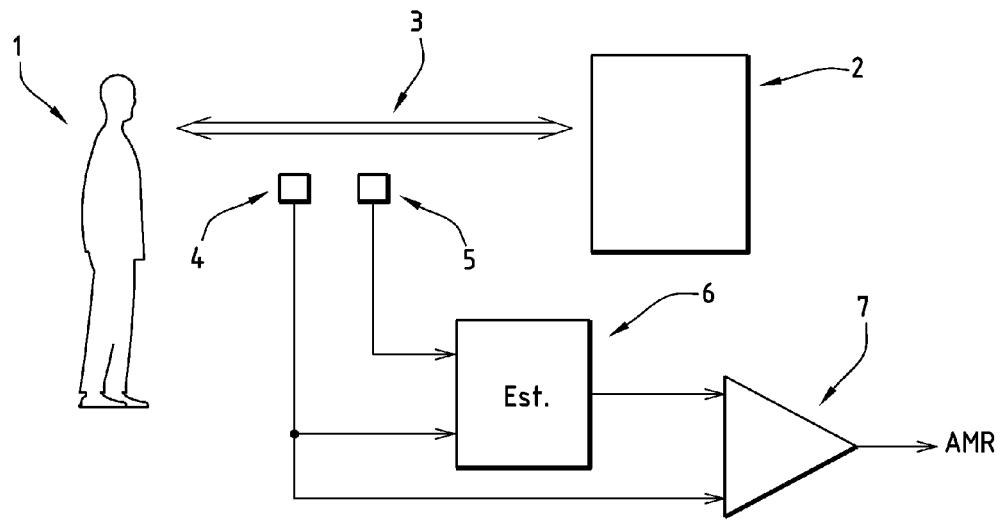

SYSTEM FOR QUANTIFYING THE DISCREPANCY BETWEEN A PATIENT RECEIVING ASSISTED BREATHING AND A CORRESPONDING ASSISTANCE DEVICE

CROSS REFERENCE TO PRIOR APPLICATIONS

This application is a U.S. National Phase application under 35 U.S.C. §371 of International Application No. PCT/FR2009/052121, filed on Nov. 3, 2009 and claims benefit of priority to French Patent Application No. 0857451, filed on Nov. 3, 2008. The International Application was published in French on Jun. 3, 2010 as WO 2010/061092 A1 under PCT Article 21(2). All of these applications are herein incorporated by reference.

The present invention relates to a system for quantifying the discrepancy between a patient receiving assisted breathing and a corresponding assistance device.

This system lies within the scope of research on the optimization of the strategies and methods for monitoring and assisting the respiratory function in anesthesia and resuscitation.

Advances in anesthesia and resuscitation have the goals of reducing the duration of the monitoring and of improving the quality of recovery of the patient.

Breathing assistance should ensure efficient and non-deleterious ventilation with acceptable comfort for the patient.

Within this context, the tuning between a patient and the corresponding breathing assistance device is decisive. In a clinical situation, the detection of a possible discrepancy is essential for optimizing the therapeutic strategy.

In the state of the art, the monitoring of the interaction between the patient and his/her breathing device comes up against the difficulty of properly estimating the breathing activity of the patient in a robust and non-invasive way.

Indeed, present non-invasive devices are regularly faulted. The limitations of these devices which are presently implemented in assistance devices are responsible for a lack of detection of the inhalation activity of the patient which causes a discrepancy between the patient and the assistance device and which is expressed by sub-optimal assistance.

Alternative devices presently available in the state of the art require sensors for measuring respiratory muscle activity, which are both invasive (intra-thoracic, needle electromyography . . . ) and not very robust either because of physiological perturbations or of the clinical course of the patient or because of the lifetime of the sensor for ensuring continuous monitoring.

Moreover, in the state of the art, there is no system with which information on the quantification of the discrepancy of the patient and the corresponding assistance device may be delivered to an operator, in a simple way, and which is directly perceptible by the operator, in order to engage a suitable correction process if necessary.

The object of the invention is therefore to solve these problems.

For this purpose, the object of the invention is a system for quantifying the discrepancy between a patient receiving breathing assistance and a corresponding assistance device, characterized in that it includes:
means for acquiring information relating to the respiratory state of the patient in a breathing cycle,
means for acquiring information relating to the operating state of the assistance device in a mechanical cycle,
means for filtering and processing this information in order to detect and localize changes in the state of the patient in a breathing cycle and of the device in a mechanical cycle,
means for calculating a piece of information on the desynchronization between the patient and the device from these changes of states, and
means forming a man/machine interface for returning this piece of desynchronization information to an operator.

According to other aspects of the invention, the quantification system comprises one or more of the following features:
the means for acquiring information relating to the respiratory state of the patient comprise means for acquiring air pressure and flow rate signals in a pneumatic circuit between the patient and the assistance device, to be sent to means for continuously estimating the theoretical pressure of the air expected in the pneumatic circuit in the absence of respiratory muscle activity of the patient and means for comparing the estimated and measured theoretical pressures in order to continuously detect a pressure difference representative of a respiratory muscle activity of the patient,
the means for acquiring information relating to the operating state of the assistance device comprise means for processing an air flow rate signal of the device for detecting the exhalation and insufflation states thereof,
the means for acquiring information relating to the operating state of the assistance device are integrated into the latter,
the means for acquiring information relating to the operating state of the assistance device comprise an airflow rate sensor associated with the pneumatic circuit between the assistance device and the patient,
the means for calculating the piece of desynchronization information comprise means for calculating a patient/machine discrepancy score according to the relationship:

$$QI(N)=H(N)-[H(B)+H(C)]$$

wherein QI(N) is the desynchronization score, (H(N) is the Shannon entropy of the assistance device+patient system, H(B) is the Shannon entropy of the patient alone and H(C) is the Shannon entropy of the assistance device alone,
the means forming a man/machine interface comprise means for displaying this score,
the display means comprise means for displaying this score in digital form,
the display means comprise means for displaying this score in graphic form,
the calculation means are adapted so as to calculate the piece of desynchronization information over a predetermined number of breathing cycles,
the estimation means comprise parameterizable and adaptive means for modeling the passive respiratory system of the patient,
the modeling means appear as models depending on at least the volume and on the air flow circulating in the pneumatic circuit.
the modeling means comprise a set of parameterizable models and in that the estimation means comprise means for extracting the measured pressure signal, input parameters of these models, in order to trigger operation of these models on the basis of these parameters and means for selecting the most discriminating model in terms of detection and non-detection of respiratory muscle activity of the patient and/or the most simple model in terms of the number of parameters used, in order to retain its estimation, the means for extracting the parameters are adapted so as to extract the parameters in at least one mechanical cycle successively consisting of one insufflation and one exhalation, while excluding the pressurization phase at the beginning of the current mechanical cycle and the phase for triggering the insufflation of the following cycle, at the end of the current mechanical cycle, the pressurization phase and the phase for triggering insufflation are detected by means for analyzing the air pressure and flow rate in the pneumatic circuit, the analysis means are connected to the means for acquiring pressure and flow rate signals in the pneumatic circuit, the analysis means are integrated into the assistance device, the phases for pressurization and for triggering insufflation are detected by analysis means from a complementary signal delivering a piece of physiological information related to the respiratory muscle activity of the patient, and the complementary signal is an electromyogram signal.

Thus, a system according to the invention gives the possibility of ensuring detection of the respiratory muscle activity of a patient receiving breathing assistance, from non-invasive measurements already available most of the time with present breathing assistance devices on the one hand, and with a method with which it is possible to circumvent the limitations related to the course of the clinical condition of the patient, of already known methods on the other hand.

Further, with such a system, it is possible through means forming a man-machine interface to return in a simple way and directly perceptible by the operator, a piece of desynchronization information so that he/she may engage the required adaptation steps.

Figure 2:
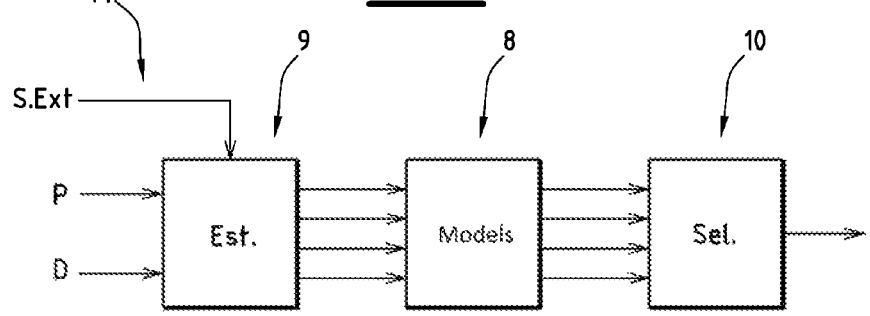
Figure 3:
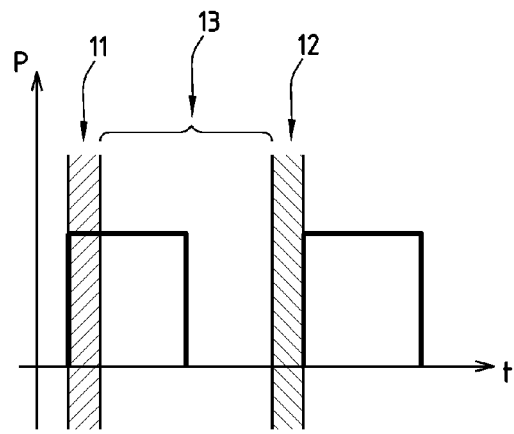
Figure 4:
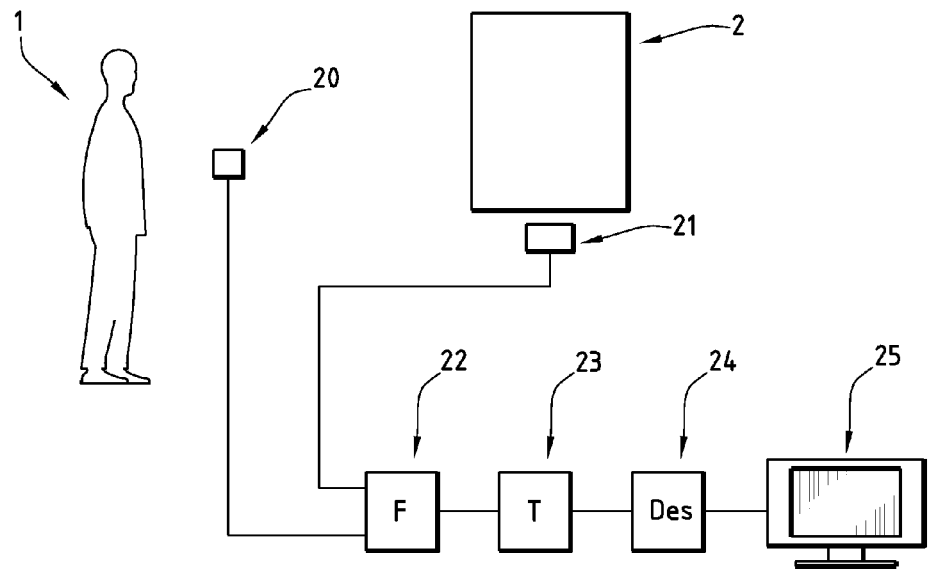
Figure 5:
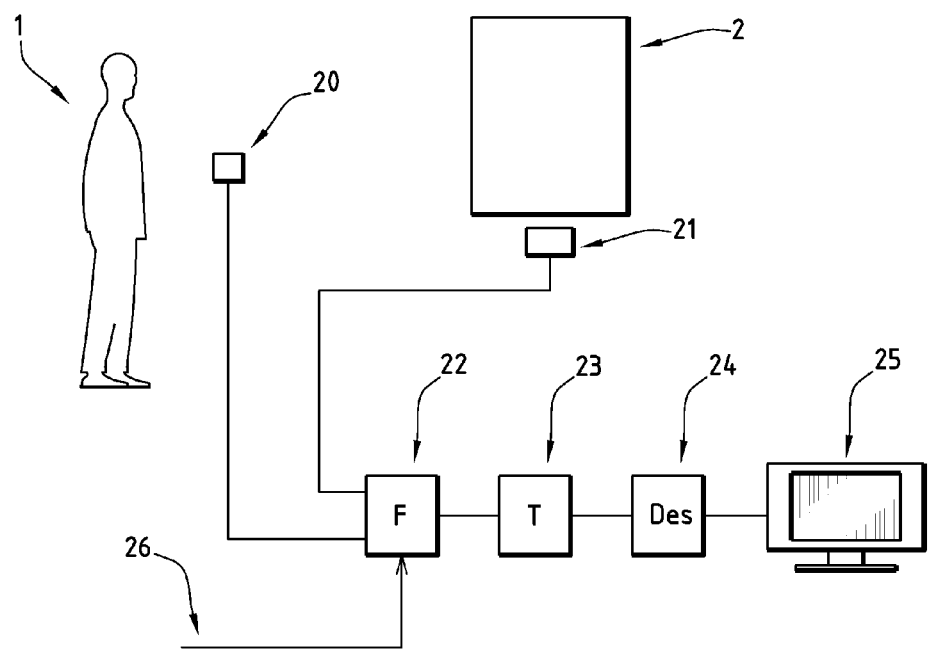
Figure 6:
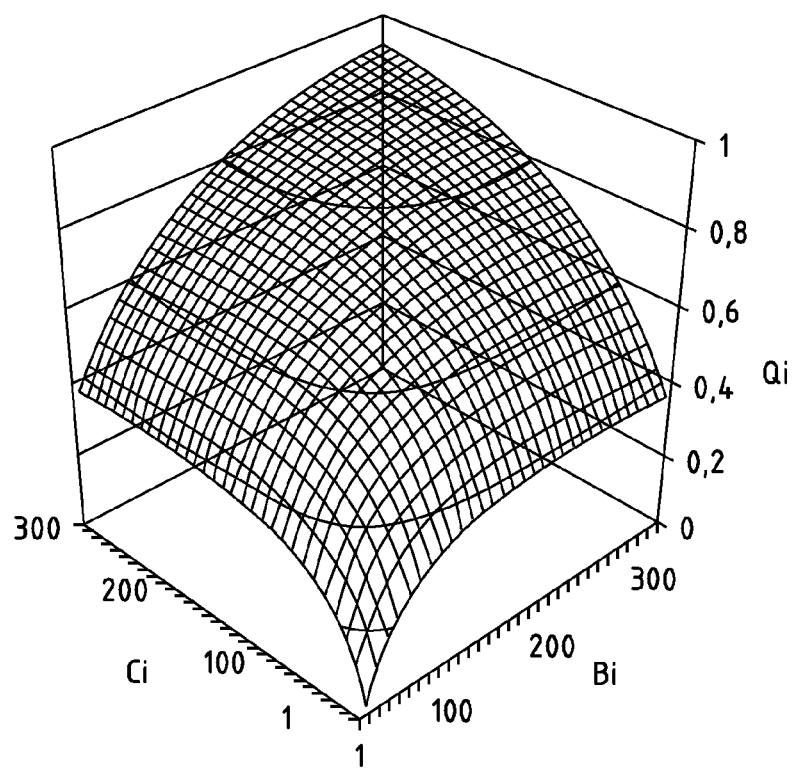

The invention will be better understood by means of the description which follows, only given as an example and made with reference to the appended drawings, wherein:

FIG. 1 illustrates a block diagram illustrating the structure and the operation of means for acquiring information relating to the respiratory state of a patient entering the set-up of a quantification system according to the invention, FIG. 2 illustrates a block diagram illustrating the structure and the operation of means for estimating pressure entering the set-up of means for acquiring information relating to the respiratory state of the patient, FIG. 3 illustrates a mechanical insufflation and exhalation cycle, FIG. 4 illustrates a block diagram illustrating the structure and the operation of a first embodiment of a quantification system according to the invention, FIG. 5 illustrates a block diagram illustrating the structure and the operation of a second embodiment of a quantification system according to the invention, and FIG. 6 illustrates the course of a patient-assistance device discrepancy.

The invention therefore relates to a system for quantifying the discrepancy between a patient receiving breathing assistance and a corresponding assistance device.

This system includes means for acquiring information relating to the respiratory state of the patient, means for acquiring information relating to the operating state of the assistance device, means for filtering and processing this information in order to detect and localize the changes in states of the patient and of the device, means for calculating a piece of information on desynchronization between the patient and the device from these state changes and means forming a man-machine interface for returning this piece of desynchronization information to an operator.

This system then aims at making available to the operator a score with which the quality of the patient-device tuning may be described in symbolic form and which may be interpreted by the operator. This score is based on a statistical analysis of the breathing cycles exhibiting desynchronization among a given number of cycles.

The principal of the quantification system is based on the calculation of the Shannon entropy of the overall patient-device system and of the dissociated sub-systems, patient on the one hand and device on the other hand. The desynchronization score then quantifies the discrepancy between the patient and his/her assistance device by the amount of additional information generated by observing a system taken as a whole with respect to the information generated by the set of sub-systems making up this overall system i.e. the patient on the one hand and the device on the other hand. This gain in information then reflects the information generated by the interaction between the investigated sub-systems.

Thus, the quantification system according to the invention therefore includes means for acquiring information relating to the respiratory state of the patient.

These means for acquiring information relating to the respiratory state of the patient are based on detection/adaptive calculation of a muscular pressure representative of the respiratory muscle activity of this patient receiving breathing assistance.

The muscular pressure may be detected or calculated from flow rate and pressure signals measured in the pneumatic circuit connecting the patient to the assistance device.

At each mechanical cycle, i.e. of the device, the parameters of a mechanical model of the passive respiratory system of the patient are identified on predetermined ranges of the breathing cycle from the flow rate signal, in order to estimate over the whole of the mechanical cycle, the expected theoretical pressure in the absence of muscular activity of the patient. The arithmetic difference between this theoretical pressure and the measured pressure is representative of the pressure generated by the respiratory muscle activity of the patient and is called the muscular pressure (Pmus). The deviation of this pressure relatively to zero indicates respiratory muscle activity which is inspiratory or expiratory depending on the sign of this deviation. By this means, the breathing cycles of the patient are identified, a breathing cycle comprising complete expiration and inspiration.

By means of such a system, it is possible to automatically adapt the parameters for calculating the muscular pressure, both to these mechanical specificities of the passive respiratory system of the patient and to the particularities of his/her breathing behavior so that continuous detection of respiratory muscle activity is as optimum as possible.

This system uses the knowledge on the triggering conditions of the insufflations in order to adapt the parameters for calculating the muscular pressure, i.e. selection of the model of the mechanics of the passive respiratory system, definition of the identification zones of the parameters of this model and selection of the thresholds for detecting muscular activity during the mechanical cycle.

Such a system is schematically illustrated in FIG. 1.

In this FIG. 1, the patient is designated by the general reference 1 and the breathing assistance device is designated by the general reference 2, the patient and the breathing device being connected through a pneumatic circuit designated by the general reference 3, in a standard way.

In the exemplary embodiment illustrated in this figure, the pneumatic circuit 3 is associated with means for acquiring air pressure and flow rate signals in this circuit, these means being designated by the references 4 and 5 respectively.

These acquisition means 4 and 5 are then adapted so as to deliver these signals to means for continuously estimating the expected theoretical pressure of the air in the pneumatic circuit in the absence of respiratory muscle activity of the patient.

These estimation means are designated by the general reference 6 in this FIG. 1 and are based on the use of parameterizable and adaptive means for modeling the passive respiratory system of the patient as this will be described in more detail subsequently.

These estimation means 6 then deliver an estimated piece of information on the theoretical pressure to comparison means designated by the general reference 7, receiving on another input the actually measured pressure in the pneumatic circuit, which allows continuous detection of a pressure difference representative of respiratory muscle activity of the patient.

In fact, and as this has been indicated earlier, the arithmetic difference between this estimated theoretical pressure and the measured pressure is representative of the pressure generated by the respiratory muscle activity of the patient and is called the muscular pressure Pmus. The deviation of this pressure relatively to zero indicates a respiratory muscle activity which is inspiratory or expiratory depending on the sign of this deviation.

As this is illustrated in FIG. 2, the modeling means of the estimation means comprise a set of parameterizable models of patient passive respiratory systems, designated by the general reference 8 in this figure. Such models are already well known in the state of the art and allow modeling of the behavior of the mechanics of the respiratory system of the patient as this will be described in more detail subsequently.

These models are parameterizable and the estimation means then comprise means for extracting the measured pressure signal, input parameters of these models so as to trigger the operation of these models on the basis of these parameters. These extraction means are designated by the general reference 9 in FIG. 2 and their operation will also be described in more detail subsequently.

The estimation means 6 also comprise means for selecting the most discriminating model in terms of detection and non-detection of respiratory muscle activity of the patient and/or the simplest model in terms of the number of parameters used, in order to retain its estimation, these selection means being designated by the general reference 10.

In fact, as this is illustrated for example in FIG. 3, the means 9 for extracting the parameters are adapted so as to extract the parameters of at least one mechanical cycle successively consisting of insufflation and exhalation for example while excluding the pressurization phase at the beginning of the current mechanical cycle and the phase for triggering the insufflation of the next cycle, at the end of the current mechanical cycle.

This is illustrated by the hatched zones in FIG. 3 where successive mechanical cycles are illustrated. The hatched zone designated by the general reference 11 in this FIG. 3 corresponds to the pressurization phase at the beginning of the current mechanical cycle while the hatched zone designated by the general reference 12, corresponds to the phase for triggering the insufflation of the next cycle, at the end of the current mechanical cycle.

The extraction of the parameters of the models is then accomplished on the zone designated by the general reference 13 between both of these exclusion zones.

Of course, different detections of these phases are possible. It is in this way for example that these phases are detected by means for analyzing the air pressure and flow rate in the pneumatic circuit, the analysis means being then connected to the means for acquiring pressure and flow rate signals in the pneumatic circuit as described earlier.

However, the analysis means may also be integrated into the assistance device directly.

Also, the phases of pressurization and insufflation triggering may also be detected by analysis means from a complementary signal delivering a piece of physiological information related to the respiratory muscle activity of the patient such as for example a complementary surface electromyogram signal as designated by the general reference 14 in FIG. 2.

With this system, it is then possible to adapt the parameters for calculating the muscular pressure, i.e. select the model of the mechanics of the passive respiratory system of the patient, define the zones for identifying the parameters of this model and the threshold for detecting a muscular activity.

The question is then to select in an adaptive way, from a set of different hierarchical models of increasing complexity, written in a for example linear form adapted to the identification of the parameters of the model, an adapted model by the multiple linear regression method and in the sense of least squares, in a standard way.

The simplest model, a so-called reference model, is a linear form with four parameters $P=f(V,D)=P_O+(V_O)*(V+(R_O+Rd*D)*D)$ with V and D corresponding to the air volume and flow rate signals versus time. The volume is calculated from the flow rate signal D by integration over time. This reference model allows efficient detection of inspiratory activities which trigger insufflation with mechanical cycle-to-cycle identification of its parameters. This identification is carried out from air flow rate and volume signals corresponding to periods of the mechanical cycle, not affected by mechanical phenomena which are not described by the model and not concerned by inspiratory muscular activity which triggers insufflation. This identification is efficient even though these identification zones are set from one patient to the other and independent of the breathing behavior of the patient. This identification zone may include two disjoint portions, one during the insufflation phase and the other one during the exhalation phase of the mechanical cycle. Still, for this reference model, with a fixed threshold for detecting a respiratory muscle activity, which is comprised between 0.5 and 2 cm $H_2O$ and preferably equal to 1 cm $H_2O$, it is possible to efficiently detect an inspiratory activity which triggers insufflation.

Other models include n-k parameters with n>k et (n−k)>4 and are also with linear forms f(V,D,A) with V,D and A which correspond to the air volume, flow rate and acceleration signals versus time. The acceleration is the first derivative of the flow rate signal D. These more complex models have the advantage of having the capability of describing mechanical phenomena which are not described by the reference model like the transition between the end of insufflation and the beginning of exhalation of the mechanical cycle.

With this capability, it is possible to propose an identification zone which is no longer disjoint but continuous, both on insufflation and on exhalation. This has two advantages:

1) A simpler definition of the identification zone by excluding a period at the end of an exhalation (or just before insufflation) defined by a far-exhalation time (Dte) and a period at the beginning of insufflation defined by a proto-insufflation time (Dpi); and 2) An improvement in the identification of the parameters of the models by taking into account the transition period between insufflation and exhalation characterized by significant changes in the flow rate and in its derivative.

Nevertheless, the increase in the complexity of the model and the extension of its capability of describing more complex mechanical phenomena potentially induces reduction in the sensitivity of the detection. Schematically, everything occurs as if transient phenomena related to muscular activity are then assigned to the mechanical characteristics of the passive respiratory system.

The system according to the invention uses a method for selecting parameters for calculating the muscular pressure which allows adaptation of the model and of the identification zone of its parameters in order to ensure efficient detection of respiratory muscle activity over the whole of the mechanical cycle.

The degradation of the performance for identifying respiratory muscle activity from the calculation of the muscular pressure with these more complex models may be efficiently compensated by suitably selecting the mechanical model and the zone for identifying the parameters of the model:
- the selected model should be as close as possible to the actual mechanics of the passive respiratory system of the patient;
- the zone for identifying the parameters should be adapted to the breathing behavior of the patient so that the excluded period of the mechanical cycle is as close as possible to the period during which the patient has inspiratory activity;
- the threshold for detecting breathing activity should be adapted depending on the quality of the adjustment of the selected model and of the identified parameters.

The adaptation principle consists of comparing the result of the identification of inspiratory activities which trigger insufflation for a set of different models and delays (Dte and Dpi) and of selecting the most adapted parameters on three criteria:

1—the capability of ensuring proper detection of known activities: the detection of insufflations detected by an inspiratory activity (Ct−(n−k)) or of an inspiratory activity which triggers insufflation (Ait−(n−k)) and which should be identical with the reference detection (Ct−ref).

2—the characteristics of an inspiration which triggers insufflation. The selective active zone is the shortest zone which precedes insufflation and for which the total duration (Dte+Dpi) is greater than or equal to the minimum duration of an inspiratory activity considered as being significant (the latter is of the order of a few tenths of a second and preferably equal to 0.3 second).

3—the properties of the models nested as a hierarchy: the selected model is the simplest model ensuring adjustment on the zone for identifying the parameters of the measured pressure, which is statistically equivalent to the most complex model (or including the most parameters).

For each combination of models and of identification zones, the result of the detection of a triggered insufflation (Ct−(n−k)) is calculated over a period of several tens of mechanical cycles (preferably 20) and is compared with the reference result (Ct−ref). Among the combinations for which the result may be superposed onto the reference result (Criterion 1), the combinations corresponding to the optimum exclusion zone (Criterion 2) are identified and then from these combinations, the optimum model is selected (Criterion 3).

With this automatic adaptation of the model, it is possible to ensure detection of the activities which trigger insufflation, at least as efficient as the validated reference method on the one hand and efficient detection of the other breathing activities present during a mechanical cycle in the case of a mismatch of the breathing activity of the patient and of its assistance device on the other hand.

This method further has the advantage of being able to continuously track both the course of the breathing behavior and of the mechanics of the respiratory system of the patient.

According to a first embodiment, the device uses the detection of the insufflations triggered by the inspiration of the patient by the reference model with four parameters. This embodiment has the advantage of reducing the input signals of the device to the sole pressure and flow rate signals.

According to a second embodiment, the information on the triggering mechanism of the insufflations are provided by an additional signal which may be provided by the assistance device or by an additional sensor. In the first case, this is a signal representative of the opening and triggering state of the insufflation valves internal to the assistance device. In the second case, this is a signal representative of the inspiratory activity of the patient provided by a non-invasive and distinct sensor sensing the pressure or flow rate signals like a detector of activity of a muscle with inspiratory activity from a surface electromyogram (sEMG or sMMG) or further a motion electromyogram (impedancemetry).

This automatic detection system was tested experimentally in three situations:
i) for evaluating the method for selecting the simplest suitable model (Criterion 3);
ii) for evaluating the method for optimally defining the identification zones (Criterion 2);
iii) for evaluating the combination of these methods.

1) Evaluation of the Method for Selecting the Simplest Suitable Model (Criterion 3):

This study was conducted from pressure and flow rate recordings made on an artificial mechanical lung ventilated with an assistance device, the mechanical characteristics of which are perfectly known. The selection method on the measured quality of the adjustment by statistical comparison of the residue leads to selecting as the simplest statistically equivalent model (with a 1% or 5% alpha risk), the minimum model required for describing the mechanics of the mechanical lung.

2) Evaluation of the Method for Optimally Defining the Identification Zones (Criterion 2):

This study was conducted from old recordings made in fourteen patients receiving partial breathing assistance who had failed a well conducted mechanical ventilation withdrawal and for this were liable to specific and invasive exploration of their breathing activity by measurement of their esophageal pressure.

In these patients, the detection capability by the non-invasive method is measured by the agreement between the activity detected by the calculation of the muscular pressure and the activity detected by reading the esophageal pressure. The value of the agreement calculated with the automatic method for selecting identification zones is compared by the method of Bland and Altman with the optimum agreement observed for the whole of the possible combinations of delays which define the identification zone and for a fixed complex model. By analyzing the graphical representation, it is possible to state that both methods are interchangeable with a low reduction of the agreement with the automatic method by 4% and a mean deviation of 4%.

In these patients, the values of optimal delays for defining the exclusion zone were identified for detecting activities which trigger insufflation and for detecting the whole of the triggering inspiratory activities or not. These optimal delays and in particular the far-exhalation delay (Dte) are directly related to the delays measured between the beginning of inspiratory activity and the triggering of insufflation defined from the esophageal pressure.

3) Evaluation of the Optimum Definition Method:

This study was conducted from old recordings made on 17 patients receiving partial breathing assistance liable to non-invasive exploration of their breathing activity by measuring a surface electromyogram of the diaphragm (sEMG). Detection of triggering or non-triggering inspiratory activities by the automatic method is compared by the method of Bland and Altman with the one provided by manual reading of the sEMG, flow rate and pressure signals. Both of these methods are superposable for detecting both types of inspiratory activities those which trigger and those which do not trigger insufflation.

It is well understood that different embodiments of such a system for detecting the breathing activity of the patient may still be contemplated.

Thus, this information relating to the respiratory state of the patient may be obtained by other means.

These acquisition means are designated by the general reference 20 in FIGS. 4 and 5, this reference generally designating all types of means for acquiring information relating to the respiratory state of the patient 1.

In these FIGS. 4 and 5, the assistance device is always designated by the general reference 2. This assistance device is itself also associated with means for acquiring information relating to its operating state.

These acquisition means are designated by the general reference 20 in these FIGS. 4 and 5 and may include means for analyzing and processing an airflow rate signal of the device in order to detect exhalation and insufflation states, from a corresponding flow rate sensor associated with the pneumatic circuit 3. These means may also be integrated to the device.

In fact, these means are intended to detect the beginning and the end of the different states of the breathing activity of the patient or of the breathing cycle and of the different activity states of the assistance device or of the mechanical cycle. With this, it is then possible to analyze the activities of the patient and of the device, both described in the form of discrete engines, characterized by different discrete states.

For the patient, these states are usually reduced to inspiration, expiration and active expiration states. For the assistance device, these states are insufflation and exhalation states. Further, the means for acquiring information relating to the operating state of the device also deliver a signal representative of the stopping mechanisms of the mechanical cycle.

The latter are indeed either triggered or not triggered by the respiratory muscle activity of the patient.

This information relating to the patient and to the device are then transmitted to filtering and real-time digital processing means for removing noise and localizing the beginnings and the ends of changes in the states of the device and of the patient, these means being respectively designated by the general references 22 and 23 in these FIGS. 4 and 5.

These means are connected to means for calculating the desynchronization information between the patient and the device from these changes in states, these calculation means being designated by the general references 24 in these FIGS. 4 and 5.

The latter then deliver after calculation a piece of desynchronization information to means forming a man-machine interface for returning the latter to an operator, these means forming an man-machine interface being designated by the general reference 25 in these FIGS. 4 and 5.

This piece of information is therefore representative of the desynchronization between the breathing device and the patient and allows quantification of this discrepancy in a way which is perceptible for an operator.

In the system according to the invention, the information on the beginnings and ends of the mechanical and breathing cycles are compared in order to define the mechanisms for stopping a state of the mechanical cycle, in order to classify the interactions defined for each breathing or mechanical cycle.

Four classes may thereby be defined:
- actively triggered stopping of the insufflation and exhalation,
- only triggering of the stopping of the exhalation,
- only triggering the stopping of the insufflation,
- absence of the stopping of either the insufflation or the exhalation.

In a first embodiment, the triggering of the mechanisms for stopping the mechanical cycle is defined on a chronological criterion. For each breathing cycle, any muscular activity continuously detected before and after beginning to stop a state of the mechanical cycle is assumed to have actively triggered this stopping mechanism.

In a second embodiment, the information on the beginnings and on the ends of the mechanical cycles and on the activity of the stopping mechanisms of the cycle are directly provided by the assistance device. In this case, the quantification system according to the invention utilizes an output of this device which provides a signal representative of the state of the internal valves which control the insufflation and exhalation as well as a signal for either triggering or not these valves by a breathing activity of the patient which is then detected by specific measurement systems integrated to the assistance device. In this case, the redundancy of the information allows an improvement in the robustness of the system.

In a third embodiment, the information on the beginnings and on the ends of the breathing cycles are processed with signals for measuring the breathing activity in addition to the flow rate and pressure signal. These may for example be electromyography signals of the respiratory muscles or further of intrathoracic pressure (esophageal or gastric pressure) which are therefore suitably conditioned by the acquisition means in order to detect the beginnings and the ends of the breathing cycles. By adding a complementary measurement signal on the breathing activity, it is possible to improve the robustness of the processing of the muscular physiological signals in order to characterize the end and the beginnings of the breathing cycle.

Such a structure is illustrated in FIG. 5 on which the complementary signal is designated by the general reference 26.

The calculation of the desynchronization score may be common to these different embodiments.

In fact, this calculation utilizes a distribution of probabilities of the classes of observable interactions for the overall system (N) and its two components i.e. the assistance device (C) and the patient (B).

This calculation takes into account the ventilation mode adjusted on the assistance device by the operator, insofar that a mode may be selected from various modes which are distinguished by their mechanism for stopping the mechanical cycle. As an example, four types of ventilation mode may be defined:

1) Controlled volume mode (VC): none of the stopping mechanisms of the cycle may be triggered by the patient,
2) Assisted controlled volume mode (VAC): the patient can only trigger the stopping of exhalation,
3) Breathing aid mode (AI): the patient may trigger both mechanisms for stopping the mechanical cycle, independently of each other,
4) A proportional assistance mode (PAV): the patient may trigger both stopping mechanisms but the stopping of insufflation can only be triggered if the mechanism for stopping exhalation has been activated beforehand.

For each mode, it is then possible to build in a standard way, the distribution of the classes of observable interactions for the system and its two components, i.e. the device and the patient.

Subsequently in the description, b will be used for designating the observed number of patient requests, c the observed number of mechanical cycles and n the whole of the observed events for the patient-device system.

In VC mode, the patient never triggers the assistance device so that there are only non-triggering inspiratory activities.

In AI mode, if the number of cycles during which both stopping mechanisms have been activated by the patient is called r0, the number of cycles for which insufflation is stopped by the patient without active stopping of the exhalation is called ri, and the number of cycles for which the exhalation is stopped by the patient without active stopping of the insufflation is called re, then the number of cycles without activation of the stopping mechanisms by the patient are:

(b−(re+ri+r0)) for breathing cycles, and (c−(re+ri+r0)) for mechanical cycles.

The probability value for each class and component of the system is estimated for a given observation time, by the ratio between the number of events of each class and the total number of events of the relevant component. The probability of the i° class of the component B, i.e. the patient, P(bi), is defined by the ratio between the cardinal number of the i° class and the number of observed events for the structure i.e. the number of breathing cycles. The probability for the whole of the system, P(bi, cj), corresponds to the probability value for simultaneous occurrence of the event of the i° class of the component B and that of the j° class of the component C. By design, the number of events of the classes corresponding to the same activation combination of the mechanisms for stopping the cycle is equal. Also, for i different from j, P(bi, cj)=0 and for i=j, P(bi, cj) is the ratio of the number of events of the class i or j divided by the number of events for the whole of the system, i.e. n=b+c−(re+ri+r0).

From the estimation of this probability distribution, the amount of information on each structure is given by the formula of the Shannon entropy H in a standard way. For the component B, it is given by the following expression:

$$H(B) = -Si\, P(bi) * \log P(bi).$$

For a system N consisting of two components B and C, the entropy H of the whole of the system N is given by:

$$H(N) = -Si\, Sj\, P(bi,cj) * \log P(bi,cj).$$

Here, as by design, for i different from j, P(bi, cj)=0, the entropy of the overall system N is given by the relationship:

$$H(N) = -Si\, Sj\, P(bi,cj) * \log P(bi,cj) = -Si\, P(bi,ci) * \log P(bi,ci) = -Si\, P(ni) * \log P(ni)$$

The gain in the amount of information generated by the constraint, in other words the quality of the transmission established between both components B and C of the system N is given by:

$$QI(N) = H(N) - [H(B) + H(C)]$$

This term represents the score of the discrepancy between the patient and the device.

Its value is positive by design.

This score provides quantification of the significance of the discrepancy between the patient and the device and preserves the essential properties of the Shannon entropy.

This score assumes values between zero and a maximum.

Its value is zero in the absence of any interaction (for example in VC where by definition the device dominates the patient and there is no interaction) or when the interaction is monotonous with a probability distribution where only one class is represented.

In the first situation, both components operate independently and the amount of information of the system H(N) are equal to the sum of the information amounts for each component so that the value of QI is zero.

In the second situation, as this is the case in mode AI or in mode VAC, when the patient triggers in a monotonous way and with always the same type of interaction, the patient-device system does not generate any information and the score is equal to zero. In the case when to each inspiration corresponds a triggered mechanical cycle, H(B)=H(C)=H(N)=0 and therefore QI(N)=0.

Conversely, if all the types of interactions are observed, the amount of information increases up to a maximum. This limit is related to the maximum of the entropy of a system which is reached when the distribution of the N classes is homogeneous (Hmax=−Log (1/N)). These properties are preserved regardless of the number of defined classes and therefore of the mechanisms triggering the cycle or the observed ventilation mode.

For its clinical validation, the score has been calculated in order to quantify the tuning between the patient and his/her assistance device on the sole criterion of the triggering of the mechanical insufflation.

This situation corresponds to the partial ventilation mode (Controlled Assisted Ventilation or Inspiratory Assistance). In this case there are only three situations, i.e.:

1) The patient request triggers the device;
2) The patient request does not trigger the device;
3) The device triggers without any patient request.

As an example, FIG. 6 illustrates the variations of the score QI with the patent-device discrepancy for 200 triggered mechanical cycles (Nt=re). The value of QI increases with the significance of the patient-device discrepancy quantified by the number of non-detected inspiratory requests and the self-triggerings of the mechanical cycles ($B_{nd}$=(b−re) and $C_{ad}$=(c−re) respectively). The value of QI is zero in the absence of any patient-device discrepancy ($C_{ad}$=$B_{nd}$=0) and switches to the value 0.84 for the situation where the numbers of non-equiprobable events are $C_{ad}$=$B_{nd}$=$N_t$=200 in order to asymptotically attain the value of 1.369:

QI is minimum (QI=0.0) in the absence of any patient-device discrepancy ($C_{ad}$=$B_{nd}$=0)

QI regularly increases with the number of events ($C_{ad}$ or $B_{nd}$). QI asymptotically tends towards a maximum when the events are equiprobable ($C_{ad}$=$B_{nd}$) and in sufficiently high number so that $N_t$ is negligible with respect to $C_{ad}$ or $B_{nd}$. In this case, P($C_{ad}$)=P($B_{nd}$)=0.5 whence H(C)=H(B)=1 and H(N)=0.631 with QI=1.369.

Also, for a given value of $C_{ad}$ or $B_{nd}$, QI increases in order to reach a maximum for $B_{nd}=N_t=200$ or $C_{ad}$. Beyond this maximum, QI remains high and close to this maximum.

It is then conceivable that the score may be displayed in digital or graphic form so as to be very simply and easily perceived by the operator, in order to engage a corrective process if necessary.

Of course it is obvious that other further embodiments may be contemplated.

The invention claimed is:

1. A system for quantifying the discrepancy between a patient receiving breathing assistance and a corresponding assistance device, comprising:
   an acquiring device acquiring information of a respiratory state of a patient over a breathing cycle,
   an information device acquiring information of an operating state of the assistance device over a mechanical cycle,
   a filter device filtering and processing this information in order to detect and localize changes in states of the patient over a breathing cycle and of the assistance device over a mechanical cycle,
   a calculator calculating a piece of information on desynchronization between the patient and the assistance device from these changes in states,
   an interface forming a man/machine interface for returning this piece of desynchronization information to an operator;
   an estimator; and
   a comparing device connected to the estimator;
   wherein the acquiring device comprises an air pressure device acquiring air pressure and flow rate signals in a pneumatic circuit between the patient and the assistance device, configured for the estimator continuously estimating the expected theoretical pressure of the air in the pneumatic circuit in the absence of respiratory muscle activity of the patient and a comparing device comparing the estimated theoretical pressure and measure pressure in order to continuously detect a pressure difference representative of respiratory muscle activity of the patient;
   wherein the calculator calculating the piece of desynchronization information comprises a discrepancy calculator calculating a patient/machine discrepancy score according to the relationship:

$$QI(N)=H(N)-[H(B)+H(C)];$$

wherein QI(N) is the desynchronization score, H(N) is the Shannon entropy of the (assistance device+patient) system, H(B) is the Shannon entropy of the patient alone, and H(C) is the Shannon entropy of the assistance device alone;
   wherein the operator does not correct the breathing cycle of the assistance device if the desynchronization score QI(N)=0, and corrects the breathing cycle of the assistance device if the desynchronization score QI(N)=1.369 or greater.

2. The quantification system according to claim 1, wherein the information device comprises an air processor processing an air flow rate signal of the assistance device in order to detect the exhalation and insufflation states of the assistance device.

3. The quantification system according to claim 1, wherein the information device relating to the operating state of the assistance device is integrated into the assistance device.

4. The quantification system according to claim 2, wherein the information device relating to the operating state of the assistance device comprise an air flow rate sensor associated with the pneumatic circuit between the assistance device and the patient.

5. The quantification system according to claim 1, the interface comprises a display displaying this discrepancy score.

6. The quantification system according to claim 1, wherein the display display displays the score in digital form.

7. The quantification system according to claim 1, the display displaying the score in graphic form.

8. The quantification system according to claim 1, wherein the calculator is adapted for calculating the piece of desynchronization information over a predetermined number of breathing cycles.

9. The quantification system according to claim 1, characterized in that the estimator comprises a modeling device parameterizable and adaptively modeling the passive respiratory system of the patient.

10. The quantification system according to claim 9, wherein the modeling device appears as models at least depending on the volume and on the flow of air circulating in the pneumatic circuit.

11. The quantification system according to claim 9 the modeling device further comprises a set of parameterizable models and in that the estimator comprises an extractor extracting a measured pressure signal, input parameters of these models, so as to trigger the operation of these models on the basis of these parameters and for a selector selecting the most discriminating model in terms of detection and non-detection of respiratory muscle activity of the patient and/or the simplest model in terms of the number of parameters used, in order to retain its estimation.

12. The quantification system according to claim 11, wherein the extractor extracting the parameters are adapted so as to extract the parameters over at least one mechanical cycle successively consisting of insufflation and exhalation, while excluding the pressurization phase at the beginning of the current mechanic cycle and the phase for triggering the insufflation of the next cycle, at the end of the current mechanical cycle.

13. The quantification system according to claim 12, wherein the pressurization phase and the phase for triggering insufflation are detected by a meter analyzing the air pressure and flow rate in the pneumatic circuit.

14. The quantification system according to claim 13, the analysis device is connected to the meter acquiring pressure and flow rate signals in the pneumatic circuit.

15. The quantification system according to claim 13, wherein the analysis device is integrated into the assistance device.

16. The quantification system according to claim 12, wherein the phases for pressurization and for triggering the insufflation are detected by the analysis device from a complementary signal delivering a piece of physiological information of the respiratory muscle activity of the patient.

17. The quantification system according to claim 16, wherein the complementary signal is an electromyogram signal.

18. A method for quantifying the discrepancy between a patient receiving breathing assistance and a corresponding assistance device, comprising the steps of:
   acquiring information of a respiratory rate of a patient over a breathing cycle, using an acquiring device,
   acquiring information of an operating state of the assistance device over a mechanical cycle using an information device, filtering an processing this information in order to detect and localize changes in states of the patient over a breathing cycle and of the assistance device over a mechanical cycle, using a filter device, calculating a piece of information on desynchronization between the patient and the assistance device from these changes in states, using a calculator, and providing a man/machine interface for returning this piece of desynchronization information to an operator, wherein the step of acquiring information by the acquiring device comprises a step of acquiring air pressure and flow rate signals in a pneumatic circuit between the patient and the assistance device using an air pressure device, and a step of delivering these acquired air pressure and flow rate signals to an estimator, and a step of continuously estimating the expected theoretical pressure of the air in the pneumatic circuit in the absence of respiratory muscle activity of the patient using the estimator, and a step of comparing the estimated theoretical pressure and a measured pressure, using a comparator device, in order to continuously detect a pressure difference representative of respiratory muscle activity of the patient;

wherein the calculator calculating the piece of desynchronization information comprises a discrepancy calculator calculating a patient/machine discrepancy score according to the relationship:

$$QI(N)=H(N)-[H(B)+H(C)];$$

wherein QI(N) is the desynchronization score, H(N) is the Shannon entropy of the (assistance device+patient) system, H(B) is the Shannon entropy of the patient alone, and H(C) is the Shannon entropy of the assistance device alone;

wherein the operator does not correct the breathing cycle of the assistance device if the desynchronization score QI(N)=0, and corrects the breathing cycle of the assistance device if the desynchronization score QI(N)=1.369 or greater.

* * * * *